United States Patent [19]

Wandell

[11] Patent Number: Plant 6,746

[45] Date of Patent: Apr. 18, 1989

[54] ENGLISH OAK NAMED 'WANDELL'

[76] Inventor: Willet N. Wandell, Rte. #1, Box 286, Oquawka, Ill. 61469

[21] Appl. No.: 123,060

[22] Filed: Nov. 19, 1987

[51] Int. Cl.[4] ..... A01H 5/00

[52] U.S. Cl. ..... Plt./51

[58] Field of Search ..... Plt./51

*Primary Examiner*—James R. Feyrer

[57] ABSTRACT

A unique *Quercus robur* denominated 'Wandell', characterized primarily by having an extremely fastigiate, upright, attractive appearance; resistance to powdery mildew; and, dense, concentrated and strongly ascending branching habit.

3 Drawing Sheets

This new variety of English Oak was discovered by me growing on cultivated property in Burlington, Iowa. The new variety has a very tight, upright, neat, symmetrical growth habit with a well groomed appearance. The fastigiate habit develops at an early age and retains the fastigiate habit with maturity. The lateral branches are strongly ascending, conforming to the shape of the crown. This type of fastigiate habit is consistantly maintained when trees are vegetatively propagated. The leaves are strongly ascending on the lateral branches and are resistant to powdery mildew common with the species.

SUMMARY OF INVENTION

A new and distinct cultivar of English oak characterized by its tight upright form that is consistantly maintained, strongly ascending branches and leaves and resistance to powdery mildew.

DESCRIPTION OF THE NEW PLANT

Figure 1:
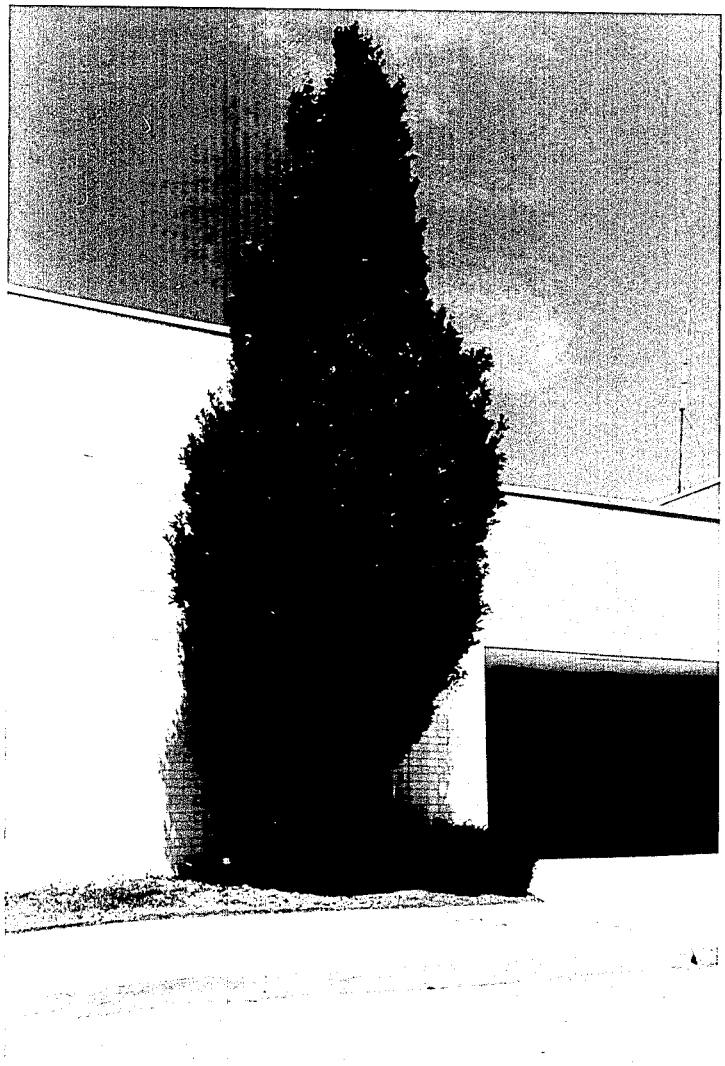
FIG. 1 is a photographic view of the tree in leaf showing its tight, neat, symmetrical, upright growth habit.
Figure 2:
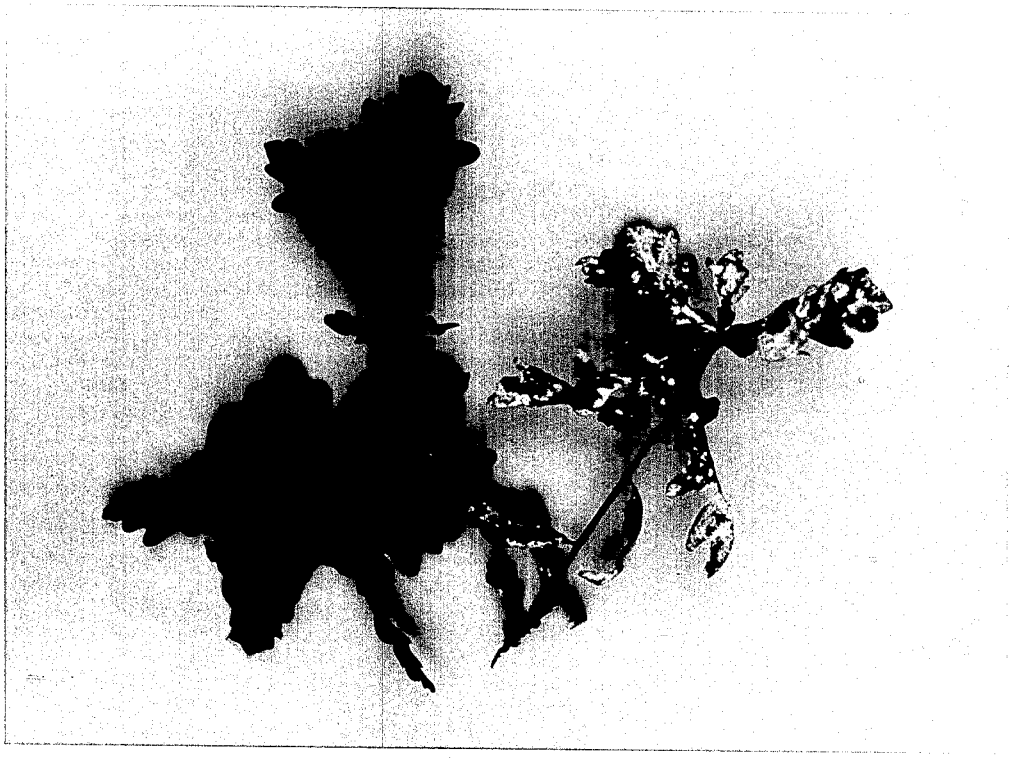
FIG. 2 is a photographic view of a comparision of the leaves of new new variety and showing the absence of powdery mildew compared to a foliage sample from a typical English oak seedling.
Figure 3:
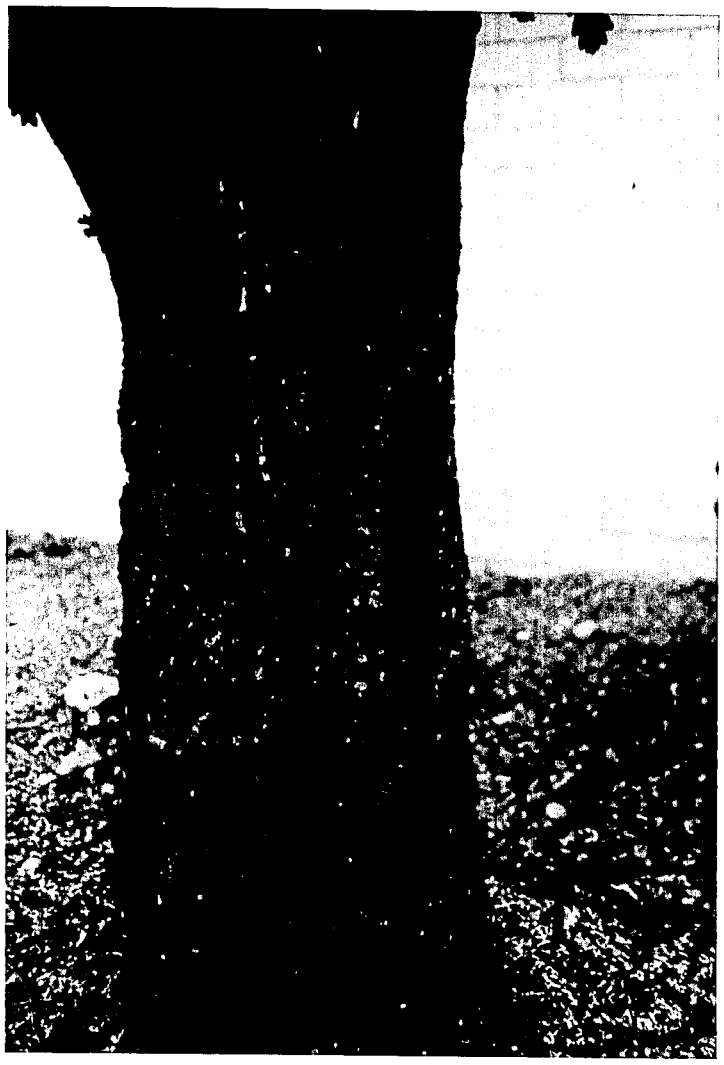
FIG. 3 is a photographic view of the bark of my new variety.
Figure 4:
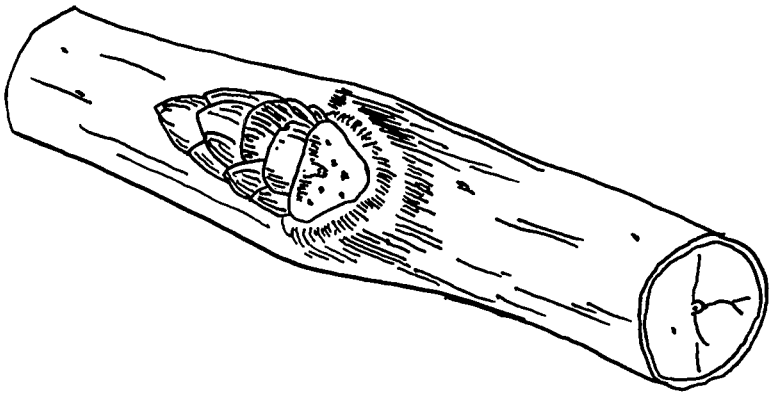
FIG. 4 is a drawing of the leaf scar of my new variety.

The following is a detailed description of my new variety with color designations according to The R.H.S. Colour Chart published by The Royal Horticultural Society of London, England and the stated observations having been made at Burlington, Iowa by applicant.

Origin: Seedling.

Parentage: A tree of unknown origin and planted in an urban site.

Propagation: Maintains its distinguishing characteristics when propagated by grafting. This tree has been asexually reproduced by myself and under my guidance by grafting.

Classification: *Quercus robur* var. 'Wandell'.

Form: Medium sized tree.

Habit: A deciduous tree with a single short trunk and a straight single leader; crown fastigiate, strongly columnar, symmetrical, near, tight and compact, with a height/width ratio of approximately 2.5 to 1; lateral branches strongly ascending, conforming to the overall shape of the crown.

Growth rate: Medium.

Bark: Dark, deeply furrowed.

Leaves: Alternate, strongly ascending on the branches, deciduous although persisting after turning brown, obovate, with 3 to 7 pairs of alternately arranged lobes, glabrous, the apices rounded, the bases shortly auriculate; petioles short, to 5 mm long.

*Size.*—6 to 11 cm long and 2.5 to 5 cm wide.

*Color.*—Dark green above (R.H.S. 137A), paler below (R.H.S. 147B).

Winter buds: Ovoid, 4 mm long, chestnut brown, with approximately 20 exposed scales, the scales fringed with short hairs.

Twigs: Fine, first year twigs 1.2 to 2.5 mm in diameter, glabrous, slightly glaucous, longitudinally grooved, greenish, becoming reddish-brown or purple, marked with buff-colored, ellipsoid lenticels. Leaf scars alternate, small, nominally 3-lobed, slightly raised, with numerous bundle traces.

Fruit: An acorn, maturing in one year, often borne in pairs, 2.5 cm long, oblong, the lower third enclosed by the shallow cup; peduncle elongate, up to 5 cm long.

Flowers: Not seen.

I claim:

1. A new and distinctive variety and the parts thereof, of *Quercus robur* named 'Wandell' as described herein, that differs from all other varieties by the unique combination of: (1) a narrow, strongly fastigiate crown that is symmetrical, tight and neat with a naturally occurring well groomed appearance; (2) this type of crown is formed on young plants, continues to mature trees, and is consistantly maintained when the plants are vegetatively propagated; and (3) the plants are resistant to powdery mildew.

* * * * *